United States Patent
Jennings et al.

(10) Patent No.: US 7,344,735 B2
(45) Date of Patent: Mar. 18, 2008

(54) METHOD FOR EXCYSTATION OF SPOROCYSTS

(75) Inventors: Neil J. Jennings, Fort Dodge, IA (US); Kirsten I. Dinka, Garner, NC (US)

(73) Assignee: Wyeth, Madison, NJ (US)

( * ) Notice: Subject to any disclaimer, the term of this patent is extended or adjusted under 35 U.S.C. 154(b) by 365 days.

(21) Appl. No.: 11/206,372

(22) Filed: Aug. 18, 2005

(65) Prior Publication Data

US 2005/0281893 A1 Dec. 22, 2005

Related U.S. Application Data

(62) Division of application No. 10/270,856, filed on Oct. 15, 2002, now Pat. No. 6,949,375.

(60) Provisional application No. 60/329,475, filed on Oct. 15, 2001.

(51) Int. Cl.
*C12Q 1/18* (2006.01)
*A61K 33/14* (2006.01)

(52) U.S. Cl. ........................ 424/661; 435/32

(58) Field of Classification Search ................ 424/661; 435/32

See application file for complete search history.

(56) References Cited

U.S. PATENT DOCUMENTS 6,344,340 B1 * 2/2002 Dibner et al. ................. 435/29

FOREIGN PATENT DOCUMENTS

WO      WO 01/15708      3/2001

OTHER PUBLICATIONS

Dubey, J.P., et al., "Sarcocystosis of Animals and Man," 1989, p. 98-99, CRC Press, Inc., Boca Raton, Florida.
Murphy, A.J., et al., "Simplified Technique for Isolation, Excystation, and Culture of Sarcocystis Species from Opossums," J. Parasitol., 1999, p. 979-981, vol. 85(5).
Cawthorn, R.J. et al., "In Vitro Excystation of Sarcocystis Capracanis Sarcocystis Cruzi and Sarcocystis Tenella," J. Parasitol., 1986, p. 880-884, vol. 72(6).
McKenna, P. B., et al., "The Survival of *Sarcocystis Gigantea* Sporocysts Following Exposure to Various Chemical and Physical Agents", Veterinary Parasitology, 1992 pp. 1-16, vol. 42.

* cited by examiner

*Primary Examiner*—Jon Weber
*Assistant Examiner*—Kailash C Srivastava
(74) *Attorney, Agent, or Firm*—Veronica Mallon

(57) ABSTRACT

A process to excystate protozoal sporocysts involves treatment of an infected tissue sample with a sodium hypochlorite solution to stimulate excystation of the sporocysts from the tissue. Thereafter, removal of the sodium hypochlorite solution and treatment of the sample with a cell culture media as the excystation fluid eliminates incubation and subsequent washing steps using expensive reagents. The excystation fluid contains substantially no chelating agents, proteins, enzymes or bile acids.

12 Claims, No Drawings

METHOD FOR EXCYSTATION OF SPOROCYSTS

This application is a divisional of application Ser. No. 10/270,856 filed Oct. 15, 2002 now U.S. Pat. No. 6,949,375, which in turn claims priority from Provisional Application Ser. No. 60/329,475, filed on Oct. 15, 2001, the entire disclosures of which are hereby incorporated by reference.

FIELD OF THE INVENTION

The present invention relates to novel methods for excystation of protozoal sporocysts, such as those of *S. neurona*, collected from mammalian tissue samples. The invention also relates to new compositions of matter which can serve as excystation fluids.

BACKGROUND OF THE INVENTION

Ingesting infective *Sarcocystis neurona* sporocysts has been determined to be the cause of equine protozoal myeloencephalitis (EPM). *S. neurona* has a host life cycle stage consisting of natural prey species, an intermediate host and a definitive host. The opossum has been determined to be the definitive host species. The feral opossum (*Didelphis virginiana*) and the South American opossum (*D. albiventris*) consume the intermediate host's muscle tissue infected with protozoal sarcocysts. Following ingestion, the protozoa undergo sexual reproduction in the intestinal epithelium of the host opossum to form oocysts. Stimulated by the intestinal environment, the oocysts undergo sporulation producing sporocysts that are eventually shed through the host opossum's feces. The speculated transmission route between opossum and equines is by fecal-oral transfer through contaminated feed or water ingested by horses.

Equines are an aberrant host because the ingested sporocysts mature into the merozoite life cycle stage but do not form sarcocysts in horse's muscle tissue. Following excystation, the sporozoites penetrate the intestinal mucosa of the horse, and undergo a series of replicative cycles in the vascular endothelial cells, and possibly in the white blood cells. The merozoites then migrate to the central nervous system where they continually divide without encysting (i.e., they do not form cysts). The merozoites divide by polygeny and often leave a residual body that gradually destroys the nervous tissue of the infected horse causing spasticity, hypermetria, ataxia, paralysis, recumbency, and death. The life-cycle stage of the protozoa that is found in horses cannot be transmitted to other horses nor can the tissue of horses, even if eaten by opossums, infect the opossum. Therefore, the horse is a dead end host for the protozoa.

The current methods of detection of EPM involve the analysis of cerebrospinal fluid for the presence of anti-*S. neurona* antibodies, as well as cytologic analysis. Antibodies are detected by an immunoblot test developed by Granstrom, D. E. (*Diagnosis of equine protozoal myeloencephalitis: Western blot analysis.* 1993. Proc. Eleventh ACVIM Forum: 587-90). Antibodies can also be detected by FIAX, a modified immunofluorescent antibody cross-reaction test. This test is performed using *Sarcocystis cruzi* bradyzoite antigen, and relies on cross-reacting antibodies. A PCR/DNA test has also been developed for detecting possible protozoal infections in the central nervous system of horses, but this test is generally not useful in the diagnosis of EPM. (Fenger C K, Granstrom D E, Langemeier J L, Stamper S. *Detection of Sarcocystis neurona in cerebrospinal fluid of horses by nested polymerase chain reaction*. J. Vet. Diagn. Invest., in press, c).

Current treatments for EPM involve the use of antibiotics that inhibit replication of the protozoa. However, there presently are no FDA or USDA approved drugs for this disease. As a consequence, there have been a number of products made available by either personal foreign importation or from off-label sources. The use of antibiotics presents two problems, a short-term course of antibiotics may only send the protozoa into remission and a long-term exposure can allow the protozoa to adapt and become resistant to the treatment. As a result, EPM prevention and treatment has become a major focus in the equine industry.

The currently available treatments for EPM are expensive, of limited efficacy, and may include adverse side effects such as anemia, abortion, diarrhea, low white blood cell counts or the like. As with most diseases, veterinary practitioners indicate that prevention of this disease is the optimal solution.

Vaccines derived from merozoites of *Sarcocystis neurona* for prevention of EPM have recently become available to protect equines against infection. To determine the efficacy of the vaccine strains, studies are conducted to determine resistivity in challenged animal models. The animals are orally exposed to the protozoa and the resultant infection is quantified by observation of clinical symptoms and examination of central nervous system tissue samples.

To quantify the viability of sporocysts, samples are excystated in vitro. Current chemical excystation methods are time consuming and involve expensive reagents that mock the harsh conditions of the intestine that are believed to stimulate sporocyst development. These procedures involve multiple washing steps because of the harsh chemicals and lengthy incubation periods, for instance, see Murphy, A. J. et al. "Simplified Technique for Isolation, Excystation, and Culture of *Sarcocystis* Species from Opossums," J. Parasitol., 1999, p. 979-981, Vol. 85(5), American Society of Parasitologists. R. J. Cawthorn et al. teaches excystation methods of *S. cruzi, S. tenella*, and *S. capracanis* in "In Vitro Excystation of *Sarcocystis capracanis, Sarcocystis cruzi* and *Sarcocystis tenella*", J. Parasitol., 1986, p. 880-884, Vol. 72(6), American Society of Parasitologists, but does not detail a generalized method for *S. neurona*. J. P. Dubey et al. in *Sarcocystis of Animals and Man,* 1989, CRC Press, Inc., Boca Raton, Fla., notes other procedures that involve expensive excystation reagents such as trypsin, bile salts, and chelating agents such as sodium ethylenediamine tetracetic acid (EDTA). Using these excystation reagents requires tedious washing of the sample to remove the excess solution in order to preserve the sporocysts.

There thus exists a need in the art for a simpler, less time-consuming, and inexpensive method for excystation of sporocysts. Also needed are new compositions that can serve as excystation fluids.

SUMMARY OF THE INVENTION

The present invention comprises a procedure for excystation of sporocysts from *Sarcocystis neurona* without the use of a chelating agent or digestive protein, enzymes or bile salts. The process involves the use of a substantially strong bleach (sodium hypochlorite—NaOCl) treatment of a suspected sample, as further described herein, to stimulate excystation of the organism from the tissue. Then, instead of treatment with a chelating agent or digestive substance, a cell culture media solution is substituted for the usual excystation fluid.

The use of cell culture media following treatment with the strong bleach solution eliminates the need for time consuming excystation incubation periods and subsequent washing steps to remove unwanted chelating or digestive agents. Using the same cell culture media solution as the excystation fluid, the sporocysts excystate and grow in the same solution. The sporocyst concentration in a sample can then be determined by counting the number of sporocysts with a hemacytometer. Additionally, an in-vitro viability measurement can be obtained from observations of S. neurona development using serial dilutions of inoculum in T-25 flasks or 96 well plates, or alternatively, the number of viable sporocysts may be estimated by a $TCID_{50}$ adapted protocol.

The foregoing and other features and advantages of the invention will become more apparent from the detailed description of the preferred embodiments of the invention given below.

DETAILED DESCRIPTION OF THE INVENTION

The process of the present invention can be applied to any tissue sample from a suspected infected animal. Initially, the samples are collected by scraping the small intestine to remove the villus. Next, the contaminated tissues are digested through conventional means using mechanical action and/or chemical means to break down the tissue and cell membranes and release additional sporocysts from the infected tissue/cells. Preferably, a laboratory blender is utilized for this purpose. Thereafter, the digested tissue samples can be stored until quantification of the protozoa is desired. However, the process of the invention may be commenced as soon as tissue digestion has been completed, thereby eliminating placing the sample in suitable storage media available in the art. If, however, the sample has been stored, the storage media is removed from the sample tissue of *S. neurona* sporocysts. A conventional method for removal of the storage media is by centrifugation of the sample at about 400×g for approximately 10-15 minutes, or until a substantially solid pellet forms.

The pellet containing the sporocysts is then resuspended in a sodium hypochlorite solution. In this way, the sporocysts are exposed to the sodium hypochlorite. By sodium hypochlorite solution it is preferably meant a commercially available 5.25% bleach solution diluted by volume with water to concentrations greater than about 1%. Other means of obtaining sodium hypochlorite solutions with concentrations greater than about 1% are also within the scope of the invention. The preferred concentrations of sodium hypochlorite solutions typically range from about 2.6%-50%, with about 15-25% being more preferred. An especially preferred sodium hypochlorite solution concentration may be at least about 20%. For many applications, a concentration of at least about 15% is preferred. The appropriate temperature of the sodium hypochlorite solution is greater than about −15° C. The preferred temperature range is from about 0° C. to 4° C., and the most preferred temperature is about 4° C. The sample is exposed to the sodium hypochlorite solution for at least about 1 minute. The preferred exposure time is about 10 to 45 minutes and the most preferred exposure time is at least about 30 minutes. Over exposure of the sample to the sodium hypochlorite solution may decrease the sporocyst's viability. Thus, an exposure time in excess of about 60 minutes is generally avoided.

After exposure to the sodium hypochlorite to stimulate the protozoa to excsystate from the sporocysts, the sample is centrifuged via conventional means until a substantially solid pellet forms and the resultant supernatant is removed. The pellet is washed with an appropriate isotonic solution at an appropriate pH level to remove excess sodium hypochlorite, and again may be centrifuged. This step of washing and centrifugation may be repeated until the excess sodium hypochlorite is removed. Removal of the sodium hypochlorite is substantially complete when little or no odor thereof is detected by the skilled artisan. Many times, a single washing will be sufficient, and often times about two washing will suffice. (Any time the pellet is resuspended in a solution, the volume of the resuspension fluid should desirably equal the original volume of the stored sample. For example, if the original stored sample volume is 50 mL, each time the sample is centrifuged and the pellet is resuspended, the volume of the resuspension fluid should also equal 50 mL.) The preferred isotonic solution is a normal saline solution containing about 8.0 grams of sodium chloride per liter of water, with optional phosphate buffering. The first saline wash is performed with about 4° C. saline solution and in any subsequent wash(es), the temperature of the saline can be increased until it reaches about 37° C. Other suitable wash solutions are also within the scope of the art.

Once the sample is washed and centrifuged, the isotonic solution, e.g. supernatant saline solution, is removed and the pellet is treated with a substantially equal volume of an appropriate excystation fluid (e.g., about 50 mL). In the prior art procedures, the next step would have been to treat the sample with an excystation fluid that might include one or more of the following: 5% cholic acid with 1% trypsin solution, $Na_2EDTA$, alkaline chelating solution (ACS), Hanks' balanced salt solution (HBSS), bovine or ovine bile, and 20% DMSO with a freeze thaw cycle. The prior art teaches that these excystation fluids require an incubation procedure. The sample must be incubated at about 37° C. and examined periodically to observe the number of sporocysts. The excystation fluid is removed when an "adequate" amount of excystation has occurred. This can take up to six hours, or even more.

Additionally, the prior art procedure requires that after incubation, the sample is centrifuged and the supernatant excystation fluid is removed by multiple washing with a cell culture media. The final step in the prior art is for the pellet to be resuspended with an appropriate growth media, which may include one or more optional antibiotics.

Advantageously, in the present invention, the time-consuming incubation and washing steps are eliminated. According to the invention, the preferred excystation procedure utilizes a cell (tissue) culture media, such as a nutrient-rich cell culture media. More desirably, a nutrient-rich cell culture media is utilized which contains at least one, and preferably two or more of the following nutrients: inorganic salts, glucose, amino acids and vitamins, as well as optional pH buffers such as HEPES (N-2-Hydroxyethylpeperazine-N'-2-ethane sulfonic acid). Inorganic salts may be chosen from the non-limiting list of the following: $Ca(NO_3)_2.4H_2O$, KCl, $MgSO_4$, NaCl, $NaHCO_3$, $Na_2HPO_4.7H_2O$. Amino acids can include glycine and the "L" versions of the following: arginine, asparagine, aspartic acid, cysteine.2HCl, glutamine, histidine, hydroxyproline, isoleucine, leucine, lysine.HCl, methionine, phenylalanine, proline, serine, threonine, tryptophan, tyrosine (as sodium salt) and valine. Useful vitamins include biotin, D-Ca pantothenate, choline chloride, folic acid, l-inositol, niacinamide, para-aminobenzoic acid, pyridoxine HCl, riboflavin, thiamine HCl, Vitamin $B_{12}$.

Preferably, RPMI 1640 media (Gibco BRL cat. #23400) is used as the excystation fluid. RPMI 1640 media, as a nutrient-rich cell culture media, contains a combination of inorganic salts, glucose, amino acids and vitamins. Other cell culture media include Minimum Essential Medium Eagle (MEM). Other excystation fluids, e.g., other cell culture media may be utilized, provided that they meet the skilled artisan's concomitant goals of substantially no incubation period and no subsequent washing steps.

As noted, after the sample is washed with the saline solution to remove excess hypochlorite solution, cell culture media, e.g., RPMI 1640 media (Gibco BRL cat. #23400), is preferably substituted as the excystation fluid. This allows the excystation incubation and washing steps of the prior art to be eliminated. In the present invention using RPMI 1640 media, the sample aliquots can be directly transferred from the sample centrifuge tube to tissue culture flasks for excystation with observation for development of *S. neurona* infection. Observation of excystation can take anywhere from several minutes to a few hours, or even longer.

Once excystation is observed, the sporozoites can be counted either by a hemacytometer, titration of a series of 10-fold sample dilutions, or via plaque formation on 96-well cell culture plates. Another method of counting is by predicting virulence from $TCID_{50}$ levels. The preferred method of quantification utilizes T-25 culture flasks because of the large confluent cell sheet that facilitates organism development. The counting methods are standard to one ordinarily skilled in the art.

The following examples illustrate various preferred aspects of the invention, but should not be construed as limiting the scope thereof.

EXAMPLES

Comparative Example 1

An unknown sample species of *Sarcocystis* (lot 1351-74-122398 opossum 183) is obtained from opossum intestine through conventional tissue digestion methods of mechanical action in a blender. The sporocysts/mL value before excystation pre-sodium hypochlorite treatment is determined by a hemocytometer to be of count $3\times10^5$ sporocysts per mL. The digested tissue sample is centrifuged at 1500 rpm for 10-15 minutes and the storage solution is removed. The remaining pellet is then treated with an equal volume of 2.6% v/v sodium hypochlorite/water solution made from 5.25% commercially available bleach. The bleach-treated sample is placed in a 0° C. to 4° C. ice/water bath for approximately 30 minutes. The sample is then centrifuged and the pellet is washed with equal volume of a normal saline solution of a concentration of 8.0 grams of sodium chloride per liter of water. This step is repeated to remove the excess sodium hypochlorite from the sample. The sample is further washed in RPMI 1640 media and then is resuspended to the original sample volume, in 10% cholic acid. The sample is incubated at 37° C. The cholic acid excystation fluid is removed by centrifugation and the pellet is washed with RPMI 1640 media. Sporocysts are quantified by conventional methods of counting plaque formations in serial dilutions of T-25 flasks, counting plaque formations in 96 well plates, or predicting virulence from $TCID_{50}$ levels. Excystation is observed at the wash steps to be of count $7\times10^4$ sporocysts per mL. During excystation, some possible excystated sporocysts are observed. After 25-day period in T-25 culture flasks containing RPMI 1640 media, no organism development is observed. After 38-day incubation period, 2 out of 4 growth culture flasks show organism development, indicating only about 50% growth, which is less than optimal.

Example 2

*S. neurona* sporocysts Lot #1470-38-081699 from bulk *S. neurona* pool 1998 collection is of count $5\times10^6$ sporocysts of *S. neurona* per mL. The method as described in Example 1 was repeated, but with the following modifications: the pre-bleach count was found to be $5\times10^5$ sporocysts per mL using a hemacytometer (dilution was 1:10); three concentrations of sodium hypochlorite solutions were used, 2.6%, 20%, and 50%; and the excystation fluid was RPMI 1640 (Gibco/BRL catalogue # 23400). Using RPMI 1640 media as the excystation fluid eliminated the necessity to incubate the samples or wash the samples after excystation. Aliquots from the sample were then directly placed in 24 well plates at room temperatures conditions. After 2.0 hours, sporozoites were observed in motion for all samples treated with different concentrations of sodium hypochlorite (bleach) solution. The results are set forth in TABLE 1 below:

TABLE 1

| Counting method | 2.6% bleach | | 20% bleach | | 50% bleach | |
|---|---|---|---|---|---|---|
| | 4.5 hrs | 22 days | 4.5 hrs | 22 days | 4.5 hrs | 22 days |
| Hemocytometer count (sporozoites/mL) | $4.1 \times 10^4$ | | $6 \times 10^4$ | | $3.25 \times 10^4$ | |
| T-25 Flasks (Plaque formation in lowest dultiton) | | $10^{-6}$ | | $10^{-6}$ | | N/A |
| 96 well plates (100 µL) (Plaque formation in lowest dultiton) | | Positive 5/6 wells in $10^{-3}$ | | Positive 5/6 wells in $10^{-3}$ | | Positive 1/6 wells in $10^{-4}$ |
| $TCID_{50}$ | | $2.5 \times 10^4$ | | $1.8 \times 10^4$ | | $3.9 \times 10^4$ |

Example 3

Samples consisted of Challenge Level *S. neurona* of count $1\times10^6$ sporocysts of *S. neurona* per mL. The pre-bleach count was $1\times10^5$ sporocysts per mL (1:10 dilution). The method as described in Example 1 was repeated except for the following modifications: the bleach solution concentrations were 2.6% and 20% and the excystation fluid was RPMI 1640 media (Gibco/BRL catalogue # 23400). Sporozoites were observed in motion after 2.0 hours but not quantified. The results of the observation are recorded in Table 2 below. Samples were observed for up to two months without any significant change in number of sporozoites. The results are shown in TABLE 2:

TABLE 2

| Counting method | 2.6% bleach | | 20% bleach | |
|---|---|---|---|---|
| | 4.0 hrs | 20 days | 4.0 hrs | 20 days |
| 24 well plates (Plaque formation in lowest dultiton) | $1.0 \times 10^4$ | | $1.1 \times 10^4$ | |
| T-25 Flasks (Plaque formation in lowest dultiton) | | $10^{-3}$ (1 plaque) | | $10^{-3}$ (multiple plaques) |
| 96 well plates (100 µL) (Plaque formation in lowest dultiton) | | Positive 1/6 wells in $10^{-4}$ | | Positive 2/6 wells in $10^{-3}$ |
| $TCID_{50}$ | | $3.9 \times 10^4$ | | $0.6 \times 10^4$ |

Example 4

Samples consisted of Challenge Level *S. neurona* of count $5 \times 10^6$ sporocysts of *S. neurona* per mL. The pre-bleach count was $5 \times 10^5$ sporocysts per mL. The method as described in Example 1 is repeated except for the following modifications: the bleach solution contained 20% bleach bulk, 10 mL sample and titrated 20% bleach, the excystation fluids were RPMI 1640, 10% cholic acid, and bovine bile. Excystation is observed after 4 hours in 24 well plates: one sporozoite observed in RPMI undiluted fluids, none in cholic acid, and none in bovine bile. The titration results in T-25 flasks 12 days post incubation are: bovine bile shows no positive flasks, cholic acid shows one positive flasks (one small plaque) at the $10^{-1}$ dilution, RPMI 1640 (growth media Antibiotic free) shows positive flasks to $10^{-2}$ dilution, RPMI 1640 (growth media with Antibiotic) shows positive flasks to $10^{-1}$ dilution, and RPMI 1640 (bleach titration growth media with Antibiotic) shows a positive flask to $10^{-1}$ dilution. This example demonstrates that the use of either cholic acid or bovine bile does not improve the method and composition of the invention.

Example 5

Three samples consisting of a measured count of $1\times10^6$ Challenge Level *S. neurona* (Sample A), a sample of *S. neurona* pool collection (Sample B), and an unknown *Sarcocystis* sporocysts quantity from an opossum (Sample C) are treated by the same method as detailed in Example 1. The merozoite count pre-bleach is found to be $1\times10^5$ sporocysts per mL for Sample A, $3.7\times10^6$ sporocysts per mL for Sample B, and $2.1\times10^6$ sporocysts per mL for Sample C. The bleach concentration is 20% bleach bulk. The excystation fluids are RPMI 1640 and 20% DMSO freeze/thaw. After five hours, sporozoites, counted in 24 well plates, are observed only in samples treated with RPMI 1640 as the excystation fluid. The titration in T-25 culture flasks 4 days later shows: Bulk *S. neurona* samples in RPMI 1640 media as the excystation fluid results in no positive flasks, bulk *S. neurona* samples in DMSO results in no positive, opossum 242 samples in RPMI 1640 media results in no positive flasks, opossum 242 samples in DMSO results in no positive flasks, challenge level sample of count $1\times10^6$ in RPMI 1640 frozen media results in no positive flasks, and a challenge level sample of count $1\times10^6$ in RPMI 1640 (not frozen) results in no positive flasks. This example demonstrates that viability of all samples was relatively low, but that only the samples treated according to the invention developed observed sporozoites.

Although the present invention has been described above in considerable detail, applicants desire the full extent of patent protection possible as defined and determined by the claims herein set forth, with reference to the above teachings but not limited to any particularly disclosed example, and in all events, consistent with the widest possible scope of the claims consistent with the spirit and scope of this application.

We claim:

1. A method of counting protozoal sporozoites in a mammalian tissue sample comprising protozoal sporocysts, comprising:

a) exposing said mammalian tissue sample to a sodium hypochlorite solution having a sodium hypochlorite concentration in a range of about 15-25% v/v for a period of up to about 45 minutes;

b) removing said sodium hypochlorite from said mammalian tissue sample by rinsing said mammalian tissue sample with a saline solution;

c) exposing said rinsed mammalian tissue sample from step (b) to an excystation fluid to affect excystation of said protozoal sporocysts to release sporozoites, wherein said excystation takes place with substantially no incubation or washing; and d) counting said sporozoites.

2. The method according to claim 1, wherein said sample is exposed to said sodium hypochlorite solution at a temperature within the range of about 0 to 4° C.

3. The method according to claim 1, wherein said sample is exposed to said sodium hypochlorite solution for a period not exceeding about 30 minutes.

4. The method according to claim 3, wherein said sample is exposed to said sodium hypochlorite solution for about 15 to 30 minutes.

5. The method according to claim 1, wherein said excystation fluid cdl culture media consists essentially of RPMI 1640 culture medium.

6. The method according to claim 1, further comprising the formation of a pellet of said mammalian tissue sample after said exposure to said sodium hypochlorite.

7. The method according to claim 6, wherein said pellet is formed via centrifugation.

8. The method according to claim 1, wherein said sporozoites formed from said excystated sporocysts from said mammalian tissue sample are counted using tissue culture flasks.

9. The method according to claim 8, wherein said mammalian tissue sample is transferred directly to said flasks prior to said counting, but after said exposure to excystation fluid to affect excystation.

10. The method according to claim 1, wherein said tissue sample is pre-digested prior to said exposure to said sodium hypochlorite.

11. The method according to claim 10, wherein said pre-digestion is undertaken using a blender.

12. The method according to claim 1, wherein said exposure to said excystation fluid is conducted using cell culture media which contain substantially no chelating agents, digestive proteins, enzymes, or bile acids.

* * * * *

UNITED STATES PATENT AND TRADEMARK OFFICE
CERTIFICATE OF CORRECTION

PATENT NO. : 7,344,735 B2  Page 1 of 1
APPLICATION NO. : 11/206372
DATED : March 18, 2008
INVENTOR(S) : Neil J. Jennings and Kirsten I. Dinka It is certified that error appears in the above-identified patent and that said Letters Patent is hereby corrected as shown below:

Col. 8, line 43, Claim 5: cdl should be cell

Signed and Sealed this

Twenty-eighth Day of July, 2009

JOHN DOLL
*Acting Director of the United States Patent and Trademark Office*